(12) United States Patent
Ibrahim et al.

(10) Patent No.: US 7,144,871 B2
(45) Date of Patent: Dec. 5, 2006

(54) PARTIAL AND FULL AGONISTS OF $A_1$ ADENOSINE RECEPTORS

(75) Inventors: Prabha Ibrahim, Mountain View, CA (US); Elfatih Elzein, Fremont, CA (US); Kevin Shenk, Palo Alto, CA (US); Robert Jiang, Mountain View, CA (US); Jeff Zablocki, Mountain View, CA (US); Xiaofen Li, Palo Alto, CA (US); Christopher Morrison, Sunnyvale, CA (US); Thao Perry, San Jose, CA (US); Dengming Xiao, Longmont, CO (US)

(73) Assignee: CV Therapeutics, Inc., Palo Alto, CA (US)

( * ) Notice: Subject to any disclaimer, the term of this patent is extended or adjusted under 35 U.S.C. 154(b) by 0 days.

(21) Appl. No.: 10/370,679

(22) Filed: Feb. 19, 2003

(65) Prior Publication Data

US 2003/0232783 A1 Dec. 18, 2003

Related U.S. Application Data

(60) Provisional application No. 60/357,961, filed on Feb. 19, 2002.

(51) Int. Cl.
*A61K 31/70* (2006.01)
*C07H 19/167* (2006.01)

(52) U.S. Cl. .................... 514/46; 536/27.23
(58) Field of Classification Search ................ 514/46; 536/27.23, 27.3
See application file for complete search history.

(56) References Cited

U.S. PATENT DOCUMENTS

| | | | |
|---|---|---|---|
| 6,258,793 B1 * | 7/2001 | Palle et al. | 514/46 |
| 6,294,522 B1 * | 9/2001 | Zablocki et al. | 514/46 |
| 6,576,619 B1 * | 6/2003 | Blackburn et al. | 514/46 |
| 6,576,620 B1 * | 6/2003 | Belardinelli et al. | 514/46 |
| 6,605,597 B1 * | 8/2003 | Zablocki et al. | 514/46 |

FOREIGN PATENT DOCUMENTS

| | | | |
|---|---|---|---|
| WO | WO 99/67262 | | 12/1999 |
| WO | WO 01/40799 A3 | * | 7/2002 |
| WO | WO 02/70532 A2 | * | 9/2002 |
| WO | WO03/070739 A1 | * | 8/2003 |

OTHER PUBLICATIONS

Dalpaiz et al. (I), "Characterization of Potential Adenosine $A_1$ Receptor Prodrugs of Adenosine Derivatives with Antiischemic Properties," *Acta Technologiae et Legis Medicamenti*, 13(1), 49-57 (2002); *Chemical Abstracts*, 138, Abstr. No. 215195, HCAPlus No. 660483 (2002); only HCAPlus Abstract supplied.*

Van Tilberg et al. (II), "5' -O-Alkyl Ethers of N,2-Substituted Adenosine Derivatives: Partial Agonists for the Adenosine $A_1$ and $A_3$ Receptors," *Journal of Medicinal Chemistry*, 44(18), 2966-2975 (Aug. 30, 2001).*

Dalpaiz et al. (II), "Synthesis and Study of 5'-Ester Prodrugs of $N^6$-Cyclopentyladenosine, a Selective $A_1$ Receptor Agonist," *Pharmaceutical Research*, 18(4), 531-536 (2001).*

Prashad et al., "Steric Effect of a Bulky Substituent at 5'-Position on the Regiospecificity of 2'- vs. 3'-O-Methylation of $N^6$-Cyclohexyladenosine," *Nucleosides & Nucleotides*, 13(4), 945-952 (1994); *Chemical Abstracts*, 122, Abstr. No. 81841, HCAPlus No. 14215 (1995); only HCAPlus Abstract supplied.*

Maillard et al., "Adenosine Receptor Prodrugs: Synthesis and Biological Activity of Derivatives of Potent, $A_1$-Selective Agonists," *Journal of Pharmaceutical Sciences*, 83(1), 46-53 (Jan., 1994).*

(W) Dhalla et al., "Pharmacology and Therapeutic Applications of A1 Adenosine Receptor Ligands," *Current Topics in Medicinal Chemistry*, 3(4), 369-385 (2003).*

Dhalla et al., "Pharmacology and Therapeutic Applications of $A_1$ Adenosine Receptor Ligands," *Current Topics in Medicinal Chemistry*, 3(4), 369-385 (2003).*

* cited by examiner

*Primary Examiner*—S. Anna Jiang
*Assistant Examiner*—L. E. Crane
(74) *Attorney, Agent, or Firm*—Brian Lewis; Pauline Ann Clarke; J. Elin Hartrum

(57) ABSTRACT

Disclosed are novel compounds that are partial and full $A_1$ adenosine receptor agonists, useful for treating various disease states, in particular tachycardia and atrial flutter, angina, myocardial infarction and hyperlipidemia.

15 Claims, No Drawings

PARTIAL AND FULL AGONISTS OF A₁ ADENOSINE RECEPTORS

The present application claims priority to Provisional U.S. patent application Ser. No. 60/357,961, filed Feb. 19, 2002, the entirety of which in incorporated herein.

FIELD OF THE INVENTION

The present invention relates to novel compounds that are partial or full $A_1$ adenosine receptor agonists, and to their use in treating mammals for various disease states, including cardiovascular diseases, in particular arrhythmia, and the prevention of sudden death resulting from arrhythmia, ischemia, CNS disorders including pain, epilepsy, emesis, and metabolic disorders including diabetes and obesity. The invention also relates to methods for their preparation, and to pharmaceutical compositions containing such compounds.

BACKGROUND

Adenosine is a naturally occurring nucleoside, which exerts its biological effects by interacting with a family of adenosine receptors known as $A_1$, $A_{2a}$, $A_{2b}$, and $A_3$, all of which modulate important physiological processes. For example, $A_{2A}$ adenosine receptors modulate coronary vasodilation, $A_{2B}$ receptors have been implicated in mast cell activation, asthma, vasodilation, regulation of cell growth, intestinal function, and modulation of neurosecretion (See Adenosine $A_{2B}$ Receptors as Therapeutic Targets, Drug Dev Res 45:198; Feoktistov et al., Trends Pharmacol Sci 19:148–153), and $A_3$ adenosine receptors modulate cell proliferation processes.

$A_1$ adenosine receptor agonists modulates the cardiostimulatory effects of catecholamine (mediated via the inhibition of adenylate cyclase), and slows the heart rate (HR) and prolongs impulse propagation through the AV node, which is due in great part to activation of $I_{KAdo}$. (B. Lerman and L. Belardinelli Circulation, Vol. 83 (1991), P 1499–1509 and J. C. Shryock and L. Belardinelli The Am. J. Cardiology, Vol. 79 (1997) P 2–10). Stimulation of the $A_1$ adenosine receptor shortens the duration and decreases the amplitude of the action potential of AV nodal cells, and hence prolongs the refractory period of the AV nodal cell. Thus, stimulation of $A_1$ receptors provides a method of treating supraventricular tachycardias, including termination of nodal re-entrant tachycardias, and control of ventricular rate during atrial fibrillation and flutter.

$A_1$ agonists are also useful for emesis, and for treating non-insulin-dependent diabetes mellitus, hyperglycemia, epilepsy (anticonvulsant activity), and provide cardio-and neuro-protection. They also have antilipolytic effects in adipocytes leading to decreased release of free fatty acids.

Accordingly, it is an object of this invention to provide compounds that are potent full $A_1$ adenosine receptor agonists or partial $A_1$ receptor agonists with a half life greater than that of adenosine. Preferred compounds of the invention are selective for the $A_1$ adenosine receptor, which minimizes undesired side effects related to stimulation or antagonism of the other adenosine receptors.

SUMMARY OF THE INVENTION

Accordingly, in a first aspect, the invention relates to compounds of Formula I:

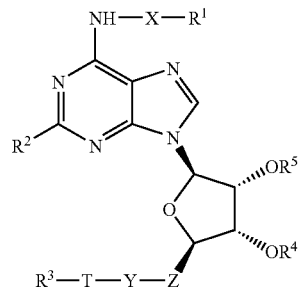

Formula I wherein:
$R^1$ is optionally substituted cycloalkyl, optionally substituted heterocyclyl, optionally substituted aryl, or optionally substituted heteroaryl;
$R^2$ is hydrogen, halo, trifluoromethyl, or cyano;
$R^3$ is optionally substituted cycloalkyl, optionally substituted aryl; optionally substituted heteroaryl, or optionally substituted heterocyclyl;
$R^4$ and $R^5$ are independently hydrogen or optionally substituted acyl;
T and X are independently a covalent bond or alkylene of 1–3 carbon atoms optionally substituted by alkyl or cycloalkyl;
Y is —O—, —NH—, —S—, or a covalent bond; and
Z is alkylene of 1–3 carbon atoms, optionally substituted by lower alkyl or cycloalkyl.

A second aspect of this invention relates to pharmaceutical formulations, comprising a therapeutically effective amount of a compound of Formula I and at least one pharmaceutically acceptable excipient.

A third aspect of this invention relates to a method of using the compounds of Formula I in the treatment of a disease or condition in a mammal that can be usefully treated with a partial or full selective $A_1$ adenosine receptor agonist. Such diseases include atrial fibrillation, supraventricular tachycardia and atrial flutter, congestive heart failure, including sudden death resulting from these conditions via the anti-lipolytic action of the compounds, ischemia, including that due to stable and unstable angina, cardiac transplantation, myocardial infarction., disorders of the CNS including epilepsy and stroke, emesis, and metabolic disorders, especially hyperlipidemia due to diabetes or obesity via the antilipolytic effect of $A_1$ agonists on adipocytes.

Definitions and General Parameters

As used in the present specification, the following words and phrases are generally intended to have the meanings as set forth below, except to the extent that the context in which they are used indicates otherwise.

The term "alkyl" refers to a monoradical branched or unbranched saturated hydrocarbon chain having from 1 to 20 carbon atoms. This term is exemplified by groups such as methyl, ethyl, n-propyl, iso-propyl, n-butyl, iso-butyl, t-butyl, n-hexyl,n-decyl, tetradecyl, and the like.

The term "substituted alkyl" refers to:

1) an alkyl group as defined above, having from 1 to 5 substituents, preferably 1 to 3 substituents, selected from the group consisting of alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocylooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may be optionally further substituted by alkyl, hydroxy, alkoxy, halogen, CF$_3$, amino, substituted amino, cyano, or —S(O)$_n$R, in which R is alkyl, aryl, or heteroaryl and n is 0, 1 or 2; or 2) an alkyl group as defined above that is interrupted by 1–5 atoms or groups independently chosen from oxygen, sulfur and —NR$_a$—, where R$_a$ is chosen from hydrogen, alkyl, cycloalkyl, alkenyl, cycloalkenyl, alkynyl, aryl, heteroaryl and heterocyclyl. All substituents may be optionally further substituted by alkyl, hydroxy, alkoxy, halogen, CF$_3$, amino, substituted amino, cyano, or —S(O)$_n$R, in which R is alkyl, aryl, or heteroaryl and n is 0, 1 or 2; or 3) an alkyl group as defined above that has both from 1 to 5 substituents as defined above and is also interrupted by 1–5 atoms or groups as defined above.

The term "lower alkyl" refers to a monoradical branched or unbranched saturated hydrocarbon chain having from 1 to 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents, preferably 1 to 3 substituents, as defined for substituted alkyl, or a lower alkyl group as defined above that is interrupted by 1–5 atoms as defined for substituted alkyl, or a lower alkyl group as defined above that has both from 1 to 5 substituents as defined aboveand is also interrupted by 1–5 atoms as defined above.

The term "alkylene" refers to a diradical of a branched or unbranched saturated hydrocarbon chain, preferably having from 1 to 20 carbon atoms, preferably 1–10 carbon atoms, more preferably 1–6 carbon atoms. This term is exemplified by groups such as methylene (—CH$_2$—), ethylene (—CH$_2$CH$_2$—), the propylene isomers (e.g., —CH$_2$CH$_2$CH$_2$— and -CH(CH$_3$)CH$_2$—) and the like.

The term "lower alkylene" refers to a diradical of a branched or unbranched saturated hydrocarbon chain, preferably having from 1 to 6 carbon atoms.

The term"substituted alkylene" refers to:

(1) an alkylene group as defined above having from 1 to 5 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocylooxy, hydroxyamino, alkoxyamino, nitro, —SO-alkyl, —SO-aryl,—SO-heteroaryl, —SO$_2$-alkyl, SO$_2$-aryl and —SO$_2$-heteroaryl. Unless otherwise constrained by the definition, all substituents may be optionally further substituted by alkyl, hydroxy, alkoxy, halogen, CF3, amino, substituted amino, cyano, or —S(O)$_n$R, in which R is alkyl, aryl, or heteroaryl and n is 0, 1 or 2; or (2) an alkylene group as defined above that is interrupted by 1–5 atoms or groups independently chosen from oxygen, sulfur and NR$_a$—, where R$_a$ is chosen from hydrogen, optionally substituted alkyl, cycloalkyl, cycloalkenyl, aryl, heteroaryl and heterocycyl, or groups selected from carbonyl, carboxyester, carboxyamide and sulfonyl; or (3) an alkylene group as defined above that has both from 1 to 5 substituents as defined above and is also interrupted by 1–20 atoms as defined above. Examples of substituted alkylenes are chloromethylene (—CH(Cl)—), aminoethylene (—CH(NH$_2$)CH$_2$—), methylaminoethylene (—CH(NHMe)CH$_2$—), 2-carboxypropylene isomers(—CH$_2$CH(CO$_2$H)CH$_2$—), ethoxyethyl (—CH$_2$CH$_2$O—CH$_2$CH$_2$—), ethylmethylaminoethyl (—CH$_2$CH$_2$N(CH$_3$)CH$_2$CH$_2$—), 1-ethoxy-2-(2-ethoxy-ethoxy)ethane (—CH$_2$CH$_2$O—CH$_2$CH$_2$—OCH$_2$CH$_2$—OCH$_2$CH$_2$—), and the like.

The term "aralkyl: refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "alkoxy" refers to the group R—O—, where R is optionally substituted alkyl or optionally substituted cycloalkyl, or R is a group —Y-Z, in which Y is optionally substituted alkylene and Z is; optionally substituted alkenyl, optionally substituted alkynyl; or optionally substituted cycloalkenyl, where alkyl, alkenyl, alkynyl, cycloalkyl and cycloalkenyl are as defined herein. Preferred alkoxy groups are alkyl-O—and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

The term "alkylthio" refers to the group R—S—, where R is as defined for alkoxy.

The term "alkenyl" refers to a monoradical of a branched or unbranched unsaturated hydrocarbon group preferably having from 2 to 20 carbon atoms, more preferably 2 to 10 carbon atoms and even more preferably 2 to 6 carbon atoms and having 1–6, preferably 1, double bond (vinyl). Preferred alkenyl groups include ethenyl or vinyl (—CH=CH$_2$), 1-propylene or allyl (—CH$_2$CH=CH$_2$), isopropylene (—C(CH$_3$)=CH$_2$), bicyclo[2.2.1]heptene, and the like. In the event that alkenyl is attached to nitrogen, the double bond cannot be alpha to the nitrogen.

The term "lower alkenyl" refers to alkenyl as defined above having from 2 to 6 carbon atoms.

The term "substituted alkenyl" refers to an alkenyl group as defined above having from 1 to 5 substituents, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocylooxy, hydroxyamino, alkoxyamino, nitro, —SO-alkyl, —SO-aryl,—SO-heteroaryl, —SO$_2$-alkyl, SO$_2$-aryl and —SO$_2$-heteroaryl. All substituents may be optionally further substituted by alkyl, hydroxy, alkoxy, halogen, CF3, amino, substituted amino, cyano, or —S(O)$_n$R, in which R is alkyl, aryl, or heteroaryl and n is 0, 1 or 2.

The term "alkynyl" refers to a monoradical of an unsaturated hydrocarbon, preferably having from 2 to 20 carbon atoms, more preferably 2 to 10 carbon atoms and even more preferably 2 to 6 carbon atoms and having at least 1 and preferably from 1–6 sites of acetylene (triple bond) unsaturation. Preferred alkynyl groups include ethynyl, (—C≡CH), propargyl (or propynyl, —C≡CCH$_3$), and the like. In the event that alkynyl is attached to nitrogen, the triple bond cannot be alpha to the nitrogen.

The term "substituted alkynyl" refers to an alkynyl group as defined above having from 1 to 5 substituents, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl,—SO-heteroaryl, —SO$_2$-alkyl, SO$_2$-aryl and —SO$_2$-heteroaryl. All substituents may be optionally further substituted by alkyl, hydroxy, alkoxy, halogen, CF3, amino, substituted amino, cyano, or —S(O)$_n$R, in which R is alkyl, aryl, or heteroaryl and n is 0, 1 or 2.

The term "aminocarbonyl" refers to the group —C(O)NRR where each R is independently hydrogen, alkyl, aryl, heteroaryl, heterocyclyl or where both R groups are joined to form a heterocyclic group (e.g., morpholino). All substituents may be optionally further substituted by alkyl, hydroxy, alkoxy, halogen, CF$_3$, amino, substituted amino, cyano, or —S(O)$_n$R, in which R is alkyl, aryl, or heteroaryl and n is 0, 1 or 2.

The term "acylamino" refers to the group —NRC(O)R where each R is independently hydrogen, alkyl, aryl, heteroaryl, or heterocyclyl. All substituents may be optionally further substituted by alkyl, hydroxy, alkoxy, halogen, CF$_3$, amino, substituted amino, cyano, or —S(O)$_n$R, in which R is alkyl, aryl, or heteroaryl and n is 0, 1 or 2.

The term "acyloxy" refers to the groups —O(O)C-alkyl, —O(O)C-cycloalkyl, —O(O)C-aryl, —O(O)C-heteroaryl, and —O(O)C-heterocyclyl. All substituents may be optionally further substituted by alkyl, hydroxy, alkoxy, halogen, CF$_3$, amino, substituted amino, cyano, or —S(O)$_n$R, in which R is alkyl, aryl, or heteroaryl and n is 0, 1 or 2.

The term "aryl" refers to an aromatic carbocyclic group of 6 to 20 carbon atoms having a single ring (e.g., phenyl) or multiple rings (e.g., biphenyl), or multiple condensed (fused) rings (e.g., naphthyl or anthryl). Preferred aryls include phenyl, naphthyl and the like.

Unless otherwise constrained by the definition for the aryl substituent, such aryl groups can optionally be substituted with from 1 to 5 substituents, preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl,—SO-heteroaryl, —SO$_2$-alkyl, SO$_2$-aryl and —SO$_2$-heteroaryl. All substituents may be optionally further substituted by alkyl, hydroxy, alkoxy, halogen, CF3, amino, substituted amino, cyano, or —S(O)$_n$R, in which R is alkyl, aryl, or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "amino" refers to the group —NH$_2$.

The term "substituted amino" refers to the group —NRR where each R is independently selected from the group consisting of hydrogen, alkyl, cycloalkyl, carboxyalkyl (for example, benzyloxycarbonyl), aryl, heteroaryl and heterocyclyl provided that both R groups are not hydrogen, or a group —Y-Z, in which Y is optionally substituted alkylene and Z is alkenyl, cycloalkenyl, or alkynyl,. All substituents may be optionally further substituted by alkyl, hydroxy, alkoxy, halogen, CF$_3$, amino, substituted amino, cyano, or —S(O)$_n$R, in which R is alkyl, aryl, or heteroaryl and n is 0, 1 or 2.

The term "carboxyalkyl" refers to the groups —C(O)O-alkyl, —C(O)O-cycloalkyl, where alkyl and cycloalkyl, are as defined herein, and may be optionally further substituted by alkyl, alkenyl, alkynyl, alkoxy, halogen, CF$_3$, amino, substituted amino, cyano, or —S(O)$_n$R, in which R is alkyl, aryl, or heteroaryl and n is 0, 1 or 2.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclohexyl, cyclooctyl, and the like, or multiple ring structures such as adamantanyl, and bicyclo[2.2.1]heptane, or cyclic alkyl groups to which is fused an aryl group, for example indan, and the like.

The term "substituted cycloalkyl" refers to cycloalkyl groups having from 1 to 5 substituents, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl,—SO-heteroaryl, —SO$_2$-alkyl, SO$_2$-aryl and —SO$_2$-heteroaryl. All substituents may be optionally further substituted by alkyl, hydroxy, alkoxy, halogen, CF3, amino, substituted amino, cyano, or —S(O)$_n$R, in which R is alkyl, aryl, or heteroaryl and n is 0, 1 or 2.

The term "halogen" or "halo" refers to fluoro, bromo, chloro, and iodo.

The term "acyl" denotes a group —C(O)R, in which R is hydrogen, optionally substituted alkyl, optionally substituted cycloalkyl, optionally substituted heterocyclyl, optionally substituted aryl, or optionally substituted heteroaryl.

The term "heteroaryl" refers to an aromatic group (i.e., unsaturated) comprising 1 to 15 carbon atoms and 1 to 4 heteroatoms selected from oxygen, nitrogen and sulfur within at least one ring.

Unless otherwise constrained by the definition for the heteroaryl substituent, such heteroaryl groups can be optionally substituted with 1 to 5 substituents, preferably 1 to 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. All substituents may be optionally further substituted by alkyl, hydroxy, alkoxy, halogen, CF3, amino, substituted amino, cyano, or —S(O)$_n$R, in which R is alkyl, aryl, or heteroaryl and n is 0, 1 or 2. Such heteroaryl groups can have a single ring (e.g., pyridyl or furyl) or multiple condensed rings (e.g., indolizinyl, benzothiazole, or benzothienyl). Examples of heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, thiazole, isothiazole, phenazine, oxazole, isoxazole, phenoxazine, phenothiazine, imidazolidine, and imidazoline.

The term "heteroaryloxy" refers to the group heteroaryl-O—.

The term "heterocyclyl" refers to a monoradical saturated or partially unsaturated group having a single ring or multiple condensed rings, having from 1 to 40 carbon atoms and from 1 to 10 hetero atoms, preferably 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl,—SO-heteroaryl, —SO$_2$-alkyl, SO$_2$-aryl and —SO$_2$-heteroaryl. All substituents may be optionally further substituted by alkyl, hydroxy, alkoxy, halogen, CF3, amino, substituted amino, cyano, or —S(O)$_n$R, in which R is alkyl, aryl, or heteroaryl and n is 0, 1 or 2. Heterocyclic groups can have a single ring or multiple condensed rings.

The term "thiol" refers to the group —SH.

The term "substituted alkylthio" refers to the group —S-substituted alkyl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, aryl, or heteroaryl. "Substituted sulfoxide" refers to a group —S(O)R, in which R is substituted alkyl, substituted aryl, or substituted heteroaryl, as defined herein.

The term "sulfone" refers to a group —S(O)$_2$R, in which R is alkyl, aryl, or heteroaryl. "Substituted sulfone" refers to a group —S(O)$_2$R, in which R is substituted alkyl, substituted aryl, or substituted heteroaryl, as defined herein.

The term "keto" refers to a group —C(O)—. The term "thiocarbonyl" refers to a group —C(S)—. The term "carboxy" refers to a group —C(O)—OH.

"Optional" or "optionally" means that the subsequently described event or circumstance may or may not occur, and that the description includes instances where said event or circumstance occurs and instances in which it does not.

The term "compound of Formula I" is intended to encompass the compounds of the invention as disclosed, and the pharmaceutically acceptable salts, pharmaceutically acceptable esters, and polymorphs and prodrugs of such compounds. Additionally, the compounds of the invention may possess one or more asymmetric centers, and can be produced as a racemic mixture or as individual enantiomers or diastereoisomers. The number of stereoisomers present in any given compound of Formula I depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis, or by resolution of the compound of Formula I by conventional means. The individual stereoisomers (including individual enantiomers and diastereoisomers) as well as racemic and non-racemic mixtures of stereoisomers are encompassed within the scope of the present invention, all of which are intended to be depicted by the structures of this specification unless otherwise specifically indicated.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn-Iigold-Prelog R—S system. When the compound is a pure enantiomer the stereochemistry at each chiral carbon may be specified by either R or S. Resolved compounds whose absolute configuration is unknown are designated (+) or (−) depending on the direction (dextro- or laevorotary) which they rotate the plane of polarized light at the wavelength of the sodium D line.

The term "therapeutically effective amount" refers to that amount of a compound of Formula I that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "treatment" or "treating" means any treatment of a disease in a mammal, including:

(i) preventing the disease, that is, causing the clinical symptoms of the disease not to develop;

(ii) inhibiting the disease, that is, arresting the development of clinical symptoms; and/or (iii) relieving the disease, that is, causing the regression of clinical symptoms.

In many cases, the compounds of this invention are capable of forming acid and/or base salts by virtue of the presence of amino and/or carboxyl groups or groups similar thereto. The term "pharmaceutically acceptable salt" refers to salts that retain the biological effectiveness and properties of the compounds of Formula I, and which are not biologically or otherwise undesirable. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

As used herein, the term "agonist" refers to the ability of a compound to interact with a receptor and evokes a maximal effect. This effect is known as the intrinsic efficacy. Many full agonists of the adenosine $A_1$ receptor are known to those skilled in the art, for example $N^6$-cyclopentyladenosine (CPA). In contrast, "partial agonists" interact with adenosine $A_1$ receptors but produce a less than maximal response.

The intrinsic efficacy of a compound may vary in different tissues. Thus, a compound may be a full agonist in a given tissue but a partial in others. The compounds identified by this invention have therapeutically useful affinities for the adenosine $A_1$ receptor but have a range of intrinsic efficacies from full agonist to partial agonist. That is, some compounds may have no effect with respect to a given effector system in a given cell type, but be a full agonist in another cell type and/or effector system. A partial agonist targeted to a selected target is likely to cause fewer side effects than a full agonist. For example, a partial $A_1$ receptor agonist may have no affect on the heart, but be potent antilipolytic compounds.

Partial $A_1$ agonists may have an added benefit for chronic therapy because they will be less likely to induce desensitization of the $A_1$ receptor (R. B. Clark, B. J. Knoll, R. Barber TiPS, Vol. 20 (1999) p. 279–286) and to cause side effects. Chronic administration of a full agonist (R-N6-phenylisopropyladenosine, R-PIA) for 7 days led to a desensitization of the $A_1$ receptor in terms of the dromotropic response in guinea pigs (note: a decrease in receptor number was observed—D. M. Dennis, J. C. Shryock, L. Belardinelli JPET, Vol. 272 (1995) p. 1024–1035). The $A_1$ agonist induced inhibitory effect on the production of cAMP by adenylate cyclase in adipocytes has been shown to desensitize upon chronic treatment with an $A_1$ agonist as well (W. J. Parsons and G. L. J. Biol. Chem. Vol. 262 (1987) p. 841–847).

NOMENCLATURE

The naming and numbering of the compounds of the invention is illustrated with a representative compound of Formula I in which $R^1$ is tetrahydrofuran-3-yl, $R^2$ is hydrogen, $R^3$ is 2-fluorophenyl, and $R^4$ and $R^5$ are both hydrogen:

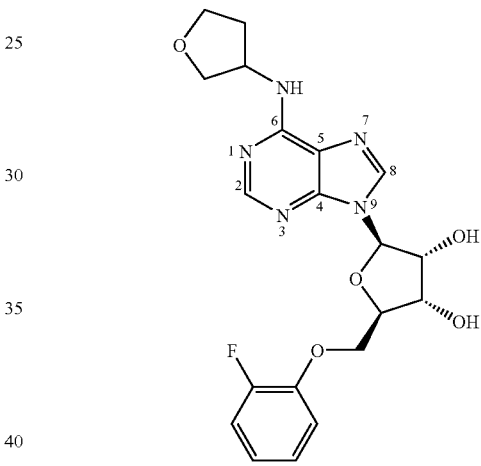

which is named: (4S,2R,3R,5R)-2-(2-fluorophenoxymethyl)]-5-[6-(tetrahydrofuran-3-ylamino)purin-9-yl]tetrahydrofuran-3.4-diol.

Synthetic Reaction Parameters

The terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents.

The term "q.s." means adding a quantity sufficient to achieve a stated function, e.g., to bring a solution to the desired volume (i.e., 100%).

SYNTHESIS OF THE COMPOUNDS OF FORMULA I

The compounds of Formula I where $R^2$ is hydrogen may be prepared starting from compound of formula (1) as shown in Reaction Scheme I.

REACTION SCHEME I

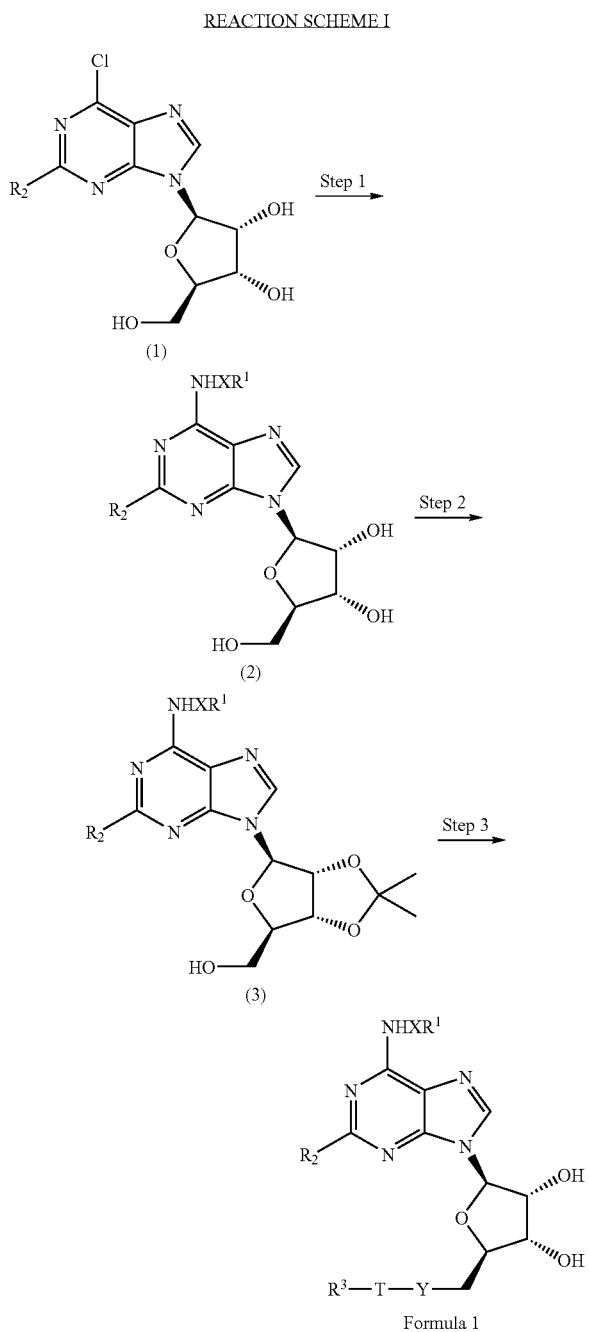

Step 1—Preparation of Formula (2)

The starting compounds of formula (1) are commercially available (for example, the compound of formula (1) in which $R^2$ is hydrogen is available from Aldrich, Milwaukee), or are prepared by means well known to those in the art. The 6-chloro moiety is displaced from the compound of formula (1) by reaction with a compound of formula $R^1XNH_2$, where X is a covalent bond or optionally substituted alkylene, in the presence of a base, preferably triethylamine. The reaction is carried out in an inert protic solvent, preferably ethanol, at a temperature of about reflux, for about 14–48 hours, preferably about 24 hours. When the reaction is substantially complete, the product of formula (2) is isolated by conventional means, for example by removal of the solvent under reduced pressure, followed by chromatography of the residue on silica gel.

Step 2—Preparation of Formula (3)

The compound of formula (3) is prepared conventionally from the compound of formula (2) by reaction with 2,2-dimethoxypropane in an inert solvent, preferably dimethylformamide, in the presence of a catalytic amount of an acid catalyst, preferably p-toluenesulfonic acid, at a temperature of about 40–90° C., preferably about 70° C., for about 24–72 hours, preferably about 48 hours. When the reaction is substantially complete, the product of formula (3) is isolated by conventional means, for example removal of the solvent under reduced pressure and purifying the residue by chromatography.

Step 3—Preparation of Formula I

To prepare a compound of Formula I where $R^3$ is aryl or heteroaryl, T is a covalent bond, and Y is —O— or —S—, the compound of formula (3) is then reacted with a compound of formula $R^3$—YH, where $R^3$ is as defined above and Y is —O— or —S—, in the presence of triphenylphosphine and a dialkylazodicarboxylate, preferably diisopropylazodicarboxylate, in an inert solvent, preferably an ether, more preferably tetrahydrofuran. The reaction is conducted at a temperature of about 40–100° C., preferably about 65° C., for about 24–100 hours, preferably about 72 hours. When the reaction is substantially complete, the product, a compound of Formula I that is protected as an acetonide, is isolated by conventional means, for example removal of the solvent under reduced pressure and purifying the residue by column chromatography.

Preparation of a compound of Formula I in which $R^3$ is cycloalkyl or heterocyclyl, or where $R^3$ is aryl or heteroaryl and T is optionally substituted alkylene, and Y is —O— or —S—, may be accomplished in the same manner as shown above. Alternatively, compounds of Formula I where Y is —O— may be prepared by reacting the compound of formula (3) with a compound of formula $R^3$-T-halo, where $R^3$ is aryl or heteroaryl and T is optionally substituted alkylene, or $R^3$ is cycloalkyl or heterocyclyl and T is a covalent bond or optionally substituted alkylene, and halo is chloro, bromo, or iodo. The reaction is carried out in the presence of a strong base, preferably potassium butoxide, and the product isolated by conventional means.

The protected compound is then converted into a compound of Formula I by treatment with an acid, preferably an organic acid, for example acetic acid. The reaction is carried out in a mixture of the acid and water, at about 50–100° C., preferably about 80–90° C., for about 10–48 hours, preferably about 16 hours. When the reaction is substantially complete, the product of Formula I is isolated by conventional means, for example by removal of the solvent under reduced pressure, followed by chromatography of the residue on silica gel.

It should be noted that steps 2 and 3 may be carried out in the reverse order.

Preparation of a Compound of Formula I in Which $R^2$ is Not Hydrogen

Preparation of a compound of Formula I in which $R^2$ is not hydrogen is shown in Reaction Scheme II.

REACTION SCHEME II

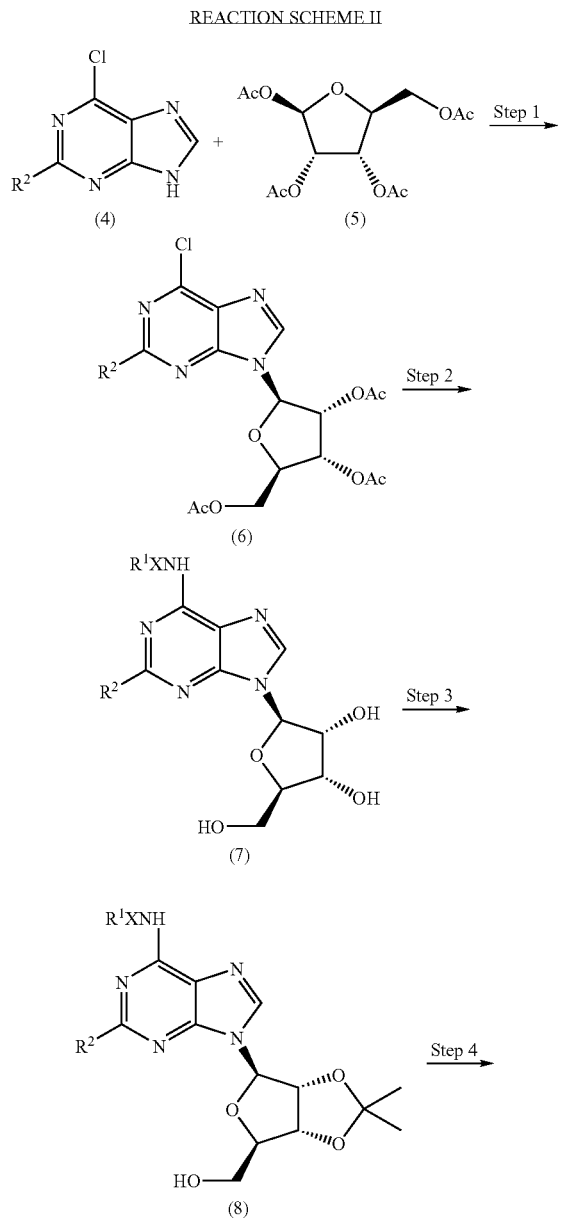

Step 1—Preparation of Formula (6)

The compound of formula (4) is commercially available, or is prepared as described below. The compound of formula (5) is commercially available (Aldrich, Milwaukee). The compounds of formula (4) and (5) are reacted to give a compound of formula (6) by conventional means well known to those skilled in the art.

Step 2—Preparation of Formula (7)

The 6-chloro moiety of the compound of formula (6) is then displaced by reaction with a compound of formula $R^1XNH$, where $R^1$ and X are as defined above, in the presence of a base, preferably triethylamine. The reaction is carried out in an inert protic solvent, preferably ethanol, at a temperature of about reflux, for about 14–48 hours, preferably about 24 hours. When the reaction is substantially complete, the product of formula (7) is isolated by conventional means, for example by removal of the solvent under reduced pressure, followed by chromatography of the residue on silica gel.

Step 3—Preparation of Formula (8)

The compound of formula (8) is prepared conventionally from the compound of formula (7) by reaction with 2,2-dimethoxypropane in an inert solvent, preferably dimethylformamide, in the presence of a catalytic amount of an acid catalyst, preferably p-toluenesulfonic acid, at a temperature of about 40–90° C., preferably about 70° C., for about 24–72 hours, preferably about 48 hours. When the reaction is substantially complete, the product of formula (8) is isolated by conventional means, for example removal of the solvent under reduced pressure and purifying the residue by flash chromatography.

Step 4—Preparation of Formula I

The compound of formula (8) is then converted to a compound of Formula I in the same manner as shown in Reaction Scheme I, step 3.

It should be noted that steps 2 and 3 may be carried out in the reverse order.

Starting Materials

Compounds of formula (4) in which $R^2$ is not hydrogen may be prepared by methods well known in the art. For example, the preparation of a compound of formula (4) in which $R^2$ is trifluoromethyl is prepared as shown in Reaction Scheme III.

REACTION SCHEME III

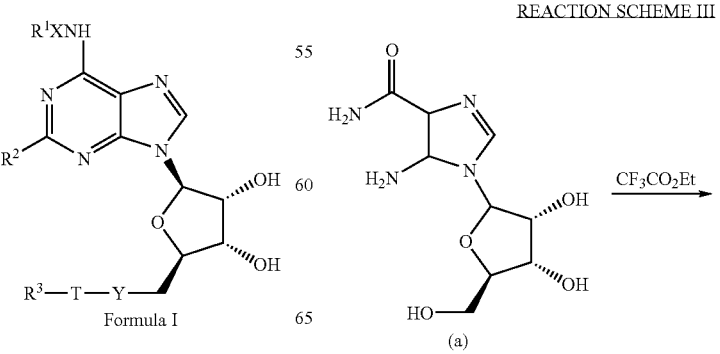

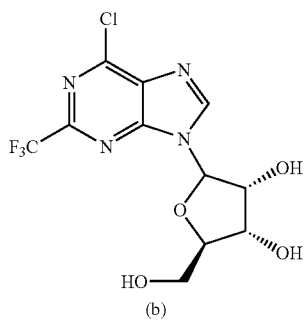

(b)

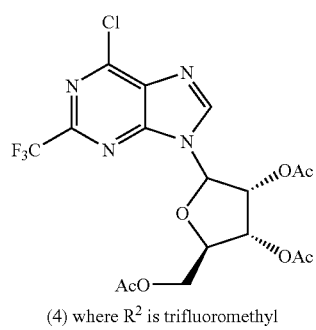

(4) where R² is trifluoromethyl

The preparation of a compound of formula (4) in which R² is nitrile is prepared as shown in Reaction Scheme W.

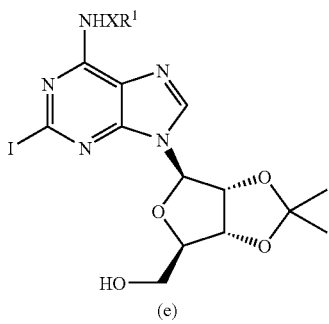

(e)

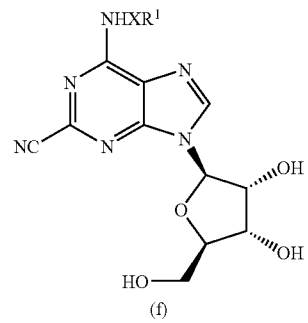

(f)

Starting Material of Formula (c)

The starting material of Formula (c) is obtained commercially (Aldrich, Milwaukee).

Preparation of a Compound in which Y is NH

The synthesis of a compound of Formula I where Y is NH is shown in Reaction Scheme V below.

REACTION SCHEME IV

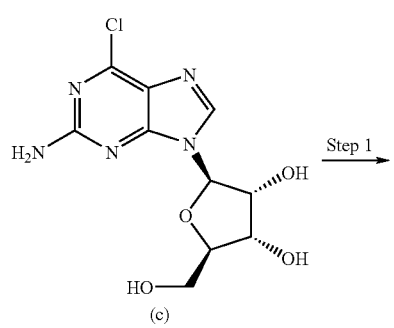

(c)

REACTION SCHEME V

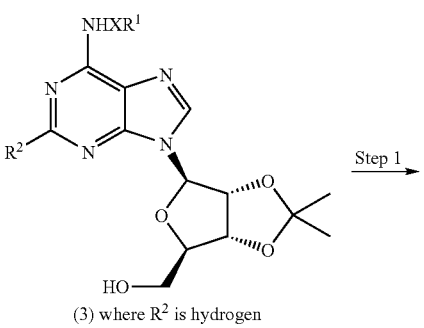

(3) where R² is hydrogen

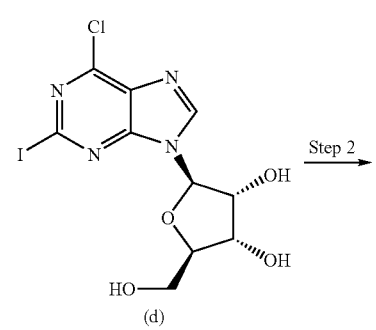

(d)

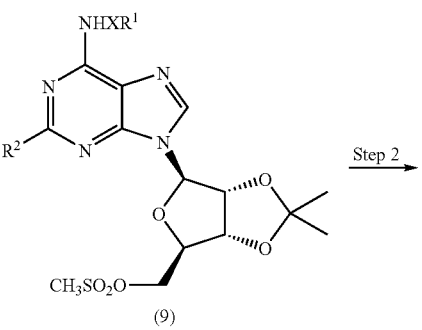

(9)

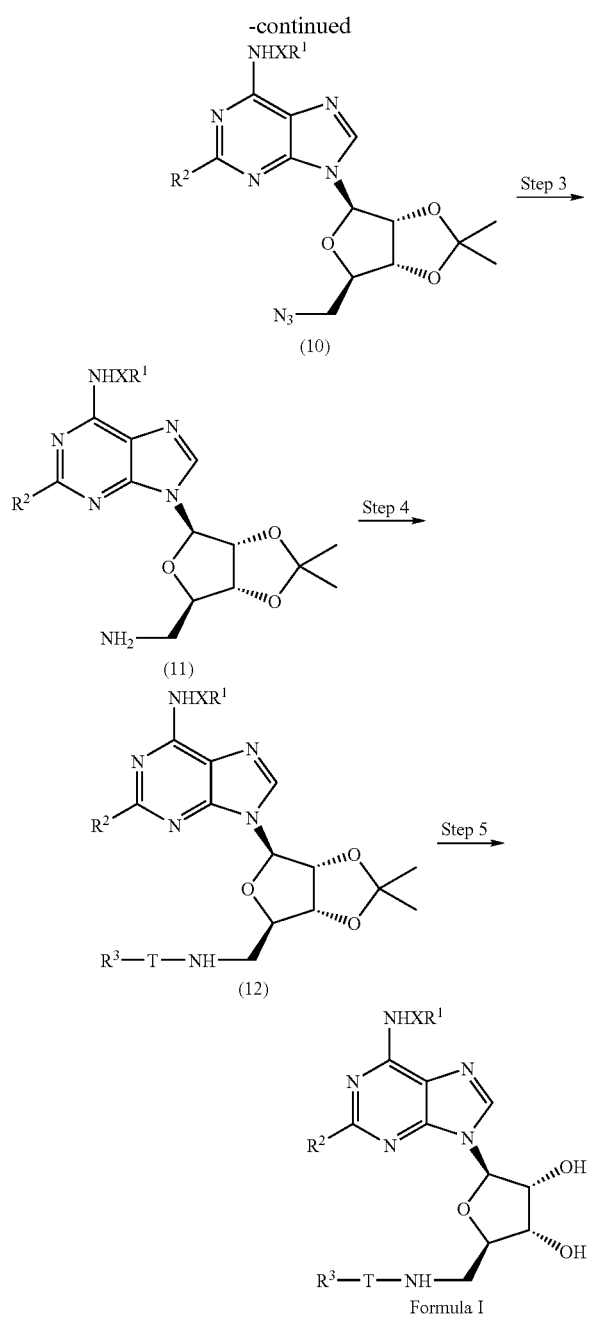

Step 1—Preparation of Formula (9)

The compound of formula (9) is prepared conventionally from the compound of formula (3), by reaction with methanesulfonyl chloride dissolved in an inert solvent for 1–3 hours at about −10° C. to 20° C. The product of formula (9) is isolated by conventional means, and used in the next reaction without further purification.

Step 2—Preparation of Formula (10).

The compound of formula (9) is converted to a compound of formula (10) by reaction with sodium azide in an inert solvent, preferably dimethylformamide, heating to 55° C. to 75° C. for 12–20 hours. When the reaction is substantially complete, the product of formula (10) is isolated by conventional means.

Step 3—Preparation of Formula (11).

The azido derivative of formula (10) is reduced to the corresponding amine by catalytic reduction, preferably using 10% PD/C in ethanol under an atmosphere of hydrogen at room temperature for 12–20 hours. When the reaction is substantially complete, the product of formula (11) is isolated by conventional means.

Step 4—Preparation of Formula (12).

The compound of formula (11) is converted to a compound of formula (12) in the same manner as shown in Reaction Scheme I, step 3.

Step 5. Preparation of a Compound of Formula 1 where Y is NH

The compound of formula (12) is converted to a compound of Formula I in the same manner as shown in Reaction Scheme I, step 3.

UTILITY, TESTING AND ADMINISTRATION

General Utility

The compounds of Formula I are effective in the treatment of conditions known to respond to administration of a partial or full agonist of an $A_1$ adenosine receptor. Such conditions include, but are not limited to, acute and chronic disorders of heart rhythm, especially those diseases characterized by rapid heart rate, in which the rate is driven by abnormalities in the sinoatrial, atria, and AV nodal tissues. Such disorders include, but are not limited to, atrial fibrillation, supraventricular tachycardia and atrial flutter, congestive heart failure and sudden death resulting from arrythmia, non-insulin-dependent diabetes mellitus, hyperglycemia, epilepsy (anti-convulsant activity), and cardio-and neuro- protection. The $A_1$ agonists of the invention also have antilipolytic effects, leading to decreased release of nonesterified fatty acids Accordingly, $A_1$ adenosine agonists are useful in the treatment of acute and chronic disorders of heart rhythm, especially those diseases characterized by rapid heart rate, in which the rate is driven by abnormalities in the sinoatrial, atria, and AV nodal tissues. Such disorders include, but are not limited to, atrial fibrillation, supraventricular tachycardia and atrial flutter. Exposure to $A_1$ agonists causes a reduction in the heart rate and a regularization of the abnormal rhythm, thereby improving cardiovascular function.

$A_1$ agonists, through their ability to inhibit the effects of catecholamines, decrease cellular cAMP, and thus have beneficial effects in the failing heart where increased sympathetic tone increases cellular cAMP levels. The latter condition has been shown to be associated with increased likelihood of ventricular arrhythmias and sudden death. See, for example, B. Lerman and L. Belardinelli Circulation, Vol. 83 (1991), P 1499–1509 and J. C. Shryock and L. Belardinelli, Am. J. Cardiology, Vol. 79 (1997) P 2–10.

$A_1$ agonists, as a result of their inhibitory action on cyclic AMP generation, have antilipolytic effects in adipocytes that leads to a decreased release of nonesterified fatty acids (NEFA) (E. A. van Schaick et al J. Pharmacokinetics and Biopharmaceutics, Vol. 25 (1997) p 673–694 and P. Strong Clinical Science Vol. 84 (1993) p. 663–669). Non-insulin-dependent diabetes mellitus (NIDDM) is characterized by an insulin resistance that results in hyperglycemia. Factors contributing to the observed hyperglycemia are a lack of normal glucose uptake and activation of skeletal muscle glycogen synthase (GS). Elevated levels of NEFA have been shown to inhibit insulin-stimulated glucose uptake and glycogen synthesis (D. Thiebaud et al Metab. Clin. Exp. Vol. 31

(1982) p 1128–1136 and G. Boden et al J. Clin. Invest. Vol. 93 (1994) p 2438–2446). The hypothesis of a glucose fatty acid cycle was proposed by P. J. Randle as early as 1963 (P. J. Randle et al Lancet (1963) p. 785–789). Thus, limiting the supply of fatty acids to the peripheral tissues promotes carbohydrate utilization (P. Strong et al Clinical Science Vol. 84 (1993) p. 663–669).

The benefit of an $A_1$ agonist in central nervous disorders has been reviewed (L. J. S. Knutsen and T. F. Murray In Purinergic Approaches in Experimental Therapeutics, Eds. K. A. Jacobson and M. F. Jarvis (1997) Wiley-Liss, N.Y., P-423–470). Briefly, based on experimental models of epilepsy, a mixed $A_{2A}$: $A_1$ agonist, metrifudil, has been shown to be a potent anticonvulsant against seizures induced by the inverse benzodiazepine agonist methyl 6,7-dimethoxy-4-ethyl-beta-carboline-3-carboxylate (DMCM, H. Klitgaard Eur. J. Pharmacol. (1993) Vol. 224 p. 221–228). In other studies using CGS 21680, an $A_{2A}$ agonist, it was concluded that the anticonvulsant activity was attributed to activation of the $A_1$ receptor (G. Zhang et al. Eur. J. Pharmacol. Vol. 255 (1994) p. 239–243). Furthermore, $A_1$ adenosine selective agonists have been shown to have anticonvulsant activity in the DMCM model (L. J. S. Knutsen In Adenosine and Adenne Nucleotides: From Molecular Biology to Integrative Physiology; eds. L. Belardinelli and A. Pelleg, Kluwer: Boston, 1995, pp 479–487). A second area where an $A_1$ adenosine agonist has a benefit is in animal models of forebrain ishemia as demonstrated by Knutsen et al (J. Med. Chem. Vol. 42 (1999) p. 3463–3477). The benefit in neuroprotection is believed to be in part due to the inhibition of the release of excitatory amino acids (ibid).

Testing

Activity testing is conducted as described in those patents and literature citations referenced above, and in the Examples below, and by methods apparent to one skilled in the art.

Pharmaceutical Compositions

The compounds of Formula I are usually administered in the form of pharmaceutical compositions. This invention therefore provides pharmaceutical compositions that contain, as the active ingredient, one or more of the compounds of Formula I, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The compounds of Formula I may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. $17^{th}$ Ed. (1985) and "Modern Pharmaceutics", Marcel Dekker, Inc. $3^{rd}$ Ed. (G. S. Banker & C. T. Rhodes, Eds.).

Administration

The compounds of Formula I may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parental, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of Formula I in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of the compounds of Formula I. Administration may be via capsule or enteric coated tablets, or the like. In making the pharmaceutical compositions that include at least one compound of Formula I, the active ingredient is usually diluted by an excipient and/or enclosed within such a carrier that can be in the form of a capsule, sachet, paper or other container. When the excipient serves as a diluent, in can be a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S.

Pat. Nos. 3,845,770; 4,326,525; 4,902514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds of Formula I are effective over a wide dosage range and is generally administered in a pharmaceutically effective amount. Preferably, for oral administration, each dosage unit contains from 10 mg to 2 g of a compound of Formula I, more preferably from 10 to 700 mg, and for parenteral administration, preferably from 10 to 700 mg of a compound of Formula I, more preferably about 50–200 mg. It will be understood, however, that the amount of the compound of Formula I actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Preparation of a Compound of Formula (2)

A. Preparation of a Compound of Formula (2) in which $R^1$ is 3-Tetrahydrofuranyl, $R^2$ is Hydrogen, and X is a Covalent Bond

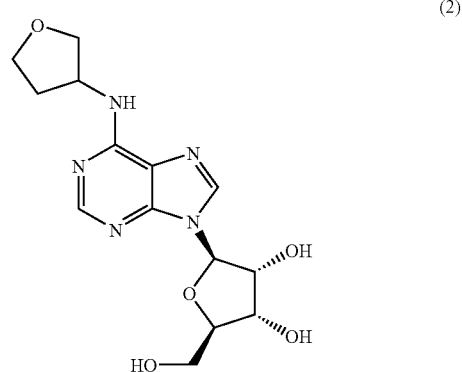

(2)

The compound of formula (2) in which R is 3-tetrahydrofuranyl, $R^2$ is hydrogen, and X is a covalent bond, namely 2-hydroxymethyl-5-[6-(tetrahydrofuran-3-ylamino)-purin-9-yl]-tetrahydrofuran-3,4-diol, is prepared as described in U.S. Pat. No. 5,789,416. For example:

1) A mixture of 3-tetrahydrofuroic acid (3.5 gm, 30 mmol), diphenylphosphorylazide (6.82 ml, 32 mmol), triethylamine (5 ml, 36 mmol) in dioxane (35 ml) was stirred at room temperature for 20 minutes, then heated in a 100° C. oil bath under dry nitrogen for 2 hours. Benzyl alcohol (4.7 ml, 45 mmol) was then added, and heating was continued at 100° C. for 22 hours. The mixture was cooled, filtered, and filtrate concentrated under reduced pressure. The residue was dissolved in 2N HCl and extracted twice with ethyl acetate. The extracts were combined and washed with water, then sodium bicarbonate, and finally brine, and dried over magnesium sulfate. The product was concentrated under reduced pressure to an oil. The oil was chromatographed on silica gel, eluting with 30% to 60% ethyl acetate/hexanes, to give 3.4 g of N-benzyloxycarbonyl-3-aminotetrahydrofuran as an oil.

2) The N-benzyloxycarbonyl-3-aminotetrahydrofuran thus prepared (3.4 gm, 15 mmol) was dissolved in methanol (50 ml) and concentrated hydrochloric acid. Pd-C (10%, 300 mg) was added, and the mixture was hydrogenated at 1 atmosphere for 18 hours at room temperature. The mixture was filtered through a pad of celite, and the filtrate concentrated under reduced pressure. The residue was co-evaporated twice with a mixture of ethyl acetate and methanol, and then recrystallized from a mixture of ethyl acetate and methanol to give 1.9 g of 3-aminotetrahydrofuran as a yellow solid.

If the starting 3-tetrahydrofuroic acid is chiral, then the product (3-aminotetrahydrofuran) is also chiral, i.e., the synthesis is stereospecific.

3. A mixture of 6-chloropurine riboside (0.5 gm, 1.74 mmol), 3-aminotetrahydrofuran (0.325 gm, 2.6 mmol) and triethylamine (0.73 ml, 5.22 mmol) in methanol (10 ml) was heated to 80° C. for 40 hours. The mixture was cooled and concentrated under reduced pressure. The residue was chromatographed on a short column of silica gel, eluting with methylene chloride/methanol/propylamine (90/10/1). The fractions containing the product were combined and concentrated under reduced pressure. The residue was chromatographed on a chromatotron (2 mm plate, 92.5/7.5/1, methylene chloride/methanol/propylamine). The resulting white solid was recrystallized from methanol/ethyl acetate to give 0.27 gm of (4S,2R, 3R,5R)-2-hydroxymethyl-5-[6-(tetrahydrofuran-3-ylamino)-purin-9-yl]-tetrahydrofuran-3,4-diol as white crystals (mp 128° C.–130° C.).

B. Preparation of a Compound of Formula (2) in which $R^1$ is Cyclopentyl, $R^2$ is Hydrogen, and X is a Covalent Bond Similarly, following the above procedures, but replacing 3-aminotetrahydrofuran with cyclopentylamine, (4S,2R,3R, 5R)-2-hydroxymethyl-5-[6-(cyclopentylamino)-purin-9-yl]-tetrahydrofuran-3,4-diol was prepared.

Similarly, the following compounds of formula (2) were prepared were:
(4S,2R,3R,5R)-2-hydroxymethyl-5-[6-(cyclohexylamino)-purin-9-yl]-tetrahydrofuran-3,4-diol;
(4S,2R,3R,5R)-2-hydroxymethyl-5-[6-(4-hydroxycyclohexylamino)-purin-9-yl]-tetrahydrofuran-3,4-diol;
(4S,2R,3R,5R)-2-hydroxymethyl-5-[6-(benzylamino)-purin-9-yl]-tetrahydrofuran-3,4-diol;
(4S,2R,3R,5R)-2-hydroxymethyl-5-[6-(4-hydroxycyclohexylamino)-purin-9-yl]-tetrahydrofuran-3,4-diol;
(4S,2R,3R,5R)-2-hydroxymethyl-5-[6-(2-benzyloxycyclopentylamino)-purin-9-yl]-tetrahydrofuran-3,4-diol;
(4S,2R,3R,5R)-2-hydroxymethyl-5-[6-(2-hydroxycyclopentylamino)-purin-9-yl]-tetrahydrofuran-3,4-diol; and
(4S,2R,3R,5R)-2-[6-({[(3-chloro(2-thienyl))methyl]propyl}amino)purin-9-yl]-5-(hydroxymethyl)oxolane-3,4-diol.

C. Preparation of Compounds of Formula (2), Varying $R^1$, $R^2$, and X

Similarly, following the procedures of Example 1A above, other compounds of formula (2) are prepared.

EXAMPLE 2

Preparation of a Compound of Formula (3)

Preparation of a Compound of Formula (3) in which $R^1$ is 3-Tetrahydrofuranyl, $R^2$ is Hydrogen, and X is a Covalent Bond

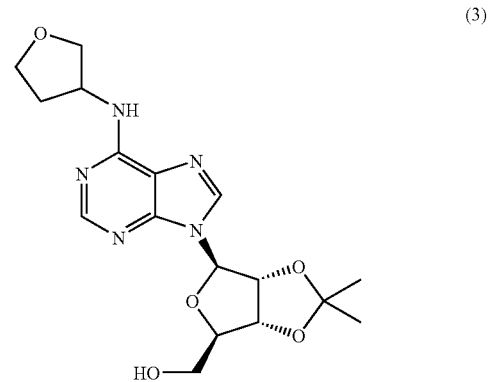

(3)

To a solution of (4S,2R,3R,5R)-2-hydroxymethyl-5-[6-(tetrahydrofuran-3-ylamino)-purin-9-yl]-tetrahydrofuran-3, 4-diol, a compound of formula (2), (2.0 g, 6.0 mmol) and 2,2-dimethoxypropane (1.2 g, 11.8 mmol) in dimethylformamide (20 mL) was added p-toluenesulfonic acid (50 mg, 0.26 mmol) at 70° C. After 48 hours at 70° C., the reaction was concentrated in vacuum to afford a solid. The solid was dissolved in methanol (3 mL), then triturated with ethyl ether (50 mL), to afford (4S,2R,3R,5R)-2-hydroxymethyl-5-[6-(tetrahydrofuran-3-ylamino)-purin-9-yl]-tetrahydrofuran-3,4-diol acetonide.

B. Preparation of a Compound of Formula (3) in which $R^1$ is Cyclopentyl, $R^2$ is Hydrogen, and X is a Covalent Bond Similarly, following the above procedure, but replacing 2-hydroxymethyl-5-[6-(tetrahydrofuran-3-ylamino)-purin-9-yl]-tetrahydrofuran-3,4-diol with 2-hydroxymethyl-5-[6-(cyclopentylamino)-purin-9-yl]-tetrahydrofuran-3,4-diol, 2-hydroxymethyl-5-[6-(cyclopentylamino)-purin-9-yl]-tetrahydrofuran-3,4-diol acetonide was prepared.

Similarly, the following compounds of formula (3) were prepared were:
(4S,2R,3R,5R)-2-hydroxymethyl-5-[6-(cyclohexylamino)-purin-9-yl]-tetrahydrofuran-3,4-diol;
(4S,2R,3R,5R)-2-hydroxymethyl-5-[6-(4-hydroxycyclohexylamino)-purin-9-yl]-tetrahydrofuran-3,4-diol acetonide;
(4S,2R,3R,5R)-2-hydroxymethyl-5-[6-(benzylamino)-purin-9-yl]-tetrahydrofuran-3,4-diol acetonide;
(4S,2R,3R,5R)-2-hydroxymethyl-5-[6-(4-hydroxycyclohexylamino)-purin-9-yl]-tetrahydrofuran-3,4-diol acetonide;
(4S,2R,3R,5R)-2-hydroxymethyl-5-[6-(2-benzyloxycyclopentylamino)-purin-9-yl]-tetrahydrofuran-3,4-diol acetonide;
(4S,2R,3R,5R)-2-hydroxymethyl-5-[6-(2-hydroxycyclopentylamino)-purin-9-yl]-tetrahydrofuran-3,4-diol acetonide; and
(4S,2R,3R,5R)-2-[6-({[(3-chloro(2-thienyl))methyl]propyl}amino)purin-9-yl]-5-(hydroxymethyl)oxolane-3, 4-diol acetonide.

C. Preparation of Compounds of Formula (3), Varying $R^1$, $R^2$, and X

Similarly, following the procedure of Example 2A above, other compounds of formula (3) are prepared.

EXAMPLE 3

Preparation of a Compound of Formula I

A. Preparation of a Compound of Formula I in which $R^1$ is 3-Tetrahydrofuranyl, $R^2$ is Hydrogen, $R^3$ is 2-Fluorophenyl, Y is Oxygen, T and X are both Covalent Bonds, and Z is Methylene

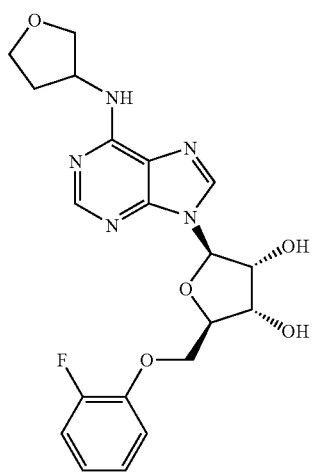

Formula I

To a solution of (4S,2R,3R,5R)-2-hydroxymethyl-5-[6-(tetrahydrofuran-3-ylamino)-purin-9-yl]-tetrahydrofuran-3,4-diol acetonide (500 mg, 1.33 mmol), 2-fluorophenol (179.4 mg, 1.6 mmol), and triphenylphospine (418.3 mg, 1.6 mmol) in anhydrous tetrahydrofuran (20 mL), DIAD (diisopropylazodicarboxylate, 320 μL, 1.6 mmol) was added and heated to reflux for 16 hours. The reaction mixture was cooled to room temperature and the solvent evaporated. The residue was purified by column chromatography (eluting with ethyl acetate: hexane 50:50) to give (4S,2R,3R,5R)-2-(2-fluorophenoxy)methyl-5-[6-(tetrahydrofuran-3-ylamino)-purin-9-yl]-tetrahydrofuran-3,4-diol acetonide as a pure white solid.

This compound was treated with 80% acetic acid/water (6 mL) and heated at 85° C. for 16 hours. The reaction mixture was cooled to room temperature and the solvent evaporated. The residue was dissolved in methanol and cooled to give the product, (4S,2R,3R,5R)-2-(2-fluorophenoxymethyl)-5-[6-(tetrahydrofuran-3-ylamino)-purin-9-yl]-tetrahydrofuran-3,4-diol, as white crystals. MS 432.1 (M+1).

B. Preparation of a Compound of Formula I in which Y is —O—, varing $R^1$, $R^2$, $R^3$, T, X, and Z Similarly, following the procedure of Example 3A above, the following compounds of Formula I in which Y is —O— were obtained:

(4S,2R,3R,5R)-2-(2-fluorophenoxymethyl)-5-[6-cyclopentylaminopurin-9-yl]-tetrahydrofuran-3,4-diol;

(4S,2R,3R,5R)-2-(2-fluorophenoxymethyl)-5-[6-cyclohexylamino)-purin-9-yl]-tetrahydrofuran-3,4-diol;

(4S,2R,3R,5R)-2-(2-chlorophenoxymethyl)-5-[6-(tetrahydrofuran-3-ylamino)-purin-9-yl]-tetrahydrofuran-3,4-diol;

(4S,2R,3R,5R)-2-(2-methylphenoxymethyl)-5-[6-(tetrahydrofuran-3-ylamino)-purin-9-yl]-tetrahydrofuran-3,4-diol;

(4S,2R,3R,5R)-2-(4-fluorophenoxymethyl)-5-[6-(tetrahydrofuran-3-ylamino)-purin-9-yl]-tetrahydrofuran-3,4-diol;

(4S,2R,3R,5R)-2-(3-fluorophenoxymethyl)-5-[6-(tetrahydrofuran-3-ylamino)-purin-9-yl]-tetrahydrofuran-3,4-diol;

(4S,2R,3R,5R)-2-(2-fluorophenoxymethyl)-5-[6-(2-benzyloxycyclopentylamino)-9-yl]-tetrahydrofuran-3,4-diol;

(4S,2R,3R,5R)-2-(2-fluorophenoxymethyl)-5-[6-(1S,2S)-(2-hydroxycyclopentylamino)-purin-9-yl]-tetrahydrofuran-3,4-diol;

(4S,2R,3R,5R)-2-(2-fluorophenoxymethyl)-5-[2-trifluoromethyl-6-(tetrahydrofuran-3-ylamino)-purin-9-yl]-tetrahydrofuran-3,4-diol;

(4S,2R,3R,5R)-2-(2-fluorophenoxymethyl)-5-[6-(4-hydroxycyclohexylamino)-purin-9-yl]-tetrahydrofuran-3,4-diol;

(4S,2R,3R,5R)-2-(2-fluorophenoxymethyl)-5-[6-(1R,2R)-(2-hydroxycyclopentylamino)-purin-9-yl]-tetrahydrofuran-3,4-diol;

(4S,2R,3R,5R)-2-(benzothiazol-2-yloxymethyl)-5-[6-(tetrahydrofuran-3-ylamino)-purin-9-yl]-tetrahydrofuran-3,4-diol;

(4S,2R,3R,5R)-2-(2-methylbenzothiazol-5-yloxymethyl)-5-[6-(tetrahydrofuran-3-ylamino)-purin-9-yl]-tetrahydrofuran-3,4-diol;

(4S,2R,3R,5R)-2-(benzoxazol-2-yloxymethyl)-5-[6-(tetrahydrofuran-3-ylamino)-purin-9-yl]-tetrahydrofuran-3,4-diol;

(4S,2R,3R,5R)-2-(pyridin-3-yloxymethyl)-5-[6-(tetrahydrofuran-3-ylamino)-purin-9-yl]-tetrahydrofuran-3,4-diol;

(4S,2R,3R,5R)-2-(benzofuran-3-onyloxymethyl)-5-[6-(tetrahydrofuran-3-ylamino)-purin-9-yl]-tetrahydrofuran-3,4-diol;

(4S,2R,3R,5R)-2-(4-quinolinyloxymethyl)-5-[6-(tetrahydrofuran-3-ylamino)-purin-9-yl]-"tetrahydrofuran-3,4-diol;"

(4S,2R,3R,5R)-2-(5-isoquinolinyloxymethyl)-5-[6-(tetrahydrofuran-3-ylamino)-purin-9-yl]-tetrahydrofuran-3,4-diol.

(4S,2R,3R,5R)-5-[6-(tetrahydrofuran-3-ylamino)purin-9-yl]-2-{[3-(trifluoromethyl)pyrazol-5-yloxy]methyl}tetrahydrofuran-3,4-diol;

(4S,2R,3R,5R)-2-[(5-methylisoxazol-3-yloxy)methyl]-5-[6-(tetrahydrofuran-3-ylamino)purin-9-yl]tetrahydrofuran-3,4-diol;

(4S,2R,3R,5R)-2-[(5-methylisoxazol-3-yloxy)methyl]-5-[6-(tetrahydrofuran-3-ylamino)purin-9-yl]tetrahydrofuran-3,4-diol;

"(4S,2R,3R,5R)-5-[(benzyloxymethyl)]2-[6-(tetrahydrofuran-3-ylamino)purin-9-yl]tetrahydrofuran-3,4-diol".

"(4S,2R,3R,5R)-5-[(2-fluorophenyloxy)methyl]-2-]6-(benzylamino)purin-9-yl]tetrahydrofuran-3,4-diol".

(4S,2R,3R,5R)-5-[(5-(2-fluorophenyloxy)methyl]-2-[6-[(3-chloro-2-thienyl)methyl]propyl}amino)purin-9-yl]tetrahydrofuran-3,4-diol;

(4S,2R,3R,5R)-2-(2-fluorophenoxymethyl)-5-[6-cyclopentylamino-purin-9-yl]-tetrahydrofuran-3,4-diol;

"(4S,2R,3R,5R)-5-[(3,5-dimethylisoxazol-4-ylthio)methyl]-2-[6-(tetrahydrofuran-3-ylamino)purin-9-yl]tetrahydrofuran-3,4-diol".

(4S,2R,3R,5R)-5-[(5-methylisoxazol-3-ylthio)methyl]-2-[6-(tetrahydrofuran-3-ylamino)purin-9-yl]tetrahydrofuran-3,4-diol;

(4S,2R,3R,5R)-2-(2-chlorophenylthiomethyl)-5-[6-cyclopentylamino-purin-9-yl]-tetrahydrofuran-3,4-diol;

(4S,2R,3R,5R)-2-[6-(cyclopentylamino)purin-9-yl]-5-[2-(phenylmethoxy)ethyl]tetrahydrofuran-3,4-diol;

(4S,2R,3R,5R)-2-[6-(cyclopentylamino)purin-9-yl]-5-[2-(2-fluoropheoxyethyl]tetrahydrofuran-3,4-diol;

"(4S,2R,3R,5R)-5-[(3-(2-chlorophenyl)isoxazol-5-ylthio)methyl]-2-[6-(cyclopentylamino)-purin-9-yl]tetrahydrofuran-3,4-diol".

"(4S,2R,3R,5R)-5-[(3-(4-chlorophenyl)isoxazol-5-ylthio)methyl]-2-[6-(cyclopentylamino)-purin-9-yl]tetrahydrofuran-3,4-diol".

(4S,2R,3R,5R)-2-[(3-(4-methoxyphenyl)isoxazol-5-ylthio)methyl]-5-[6-(cyclopentylamino)-purin-9-yl]tetrahydrofuran-3,4-diol;

(4S,2R,3R,5R)-2-[1,2,4-oxadiazol-3-ylthio)methyl]-5-[6-(cyclopentylamino)-purin-9-yl]tetrahydrofuran-3,4-diol;

(4S,2R,3R,5R)-2-[1,2,4-oxadiazol-3-yloxy)methyl]-5-[6-(cyclopentylamino)-purin-9-yl]tetrahydrofuran-3,4-diol;

"(4S,2R,3R,5R)-5-[(3,5-dimethylisoxazol-4-yloxy)methyl]-2-[6-(cyclopentylamino)purin-9-yl]tetrahydrofuran-3,4-diol".

"(4S,2R,3R,5R)-5-[(5-methylisoxazol-3-yloxy)methyl]-2-[6-(cyclopentylamino)purin-9-yl]tetrahydrofuran-3,4-diol".

"(4S,2R,3R,5R)-5-[(2-chlorophenoxy)methyl]-2-[6-(cyclopentylamino)purin-9-yl]tetrahydrofuran-3,4-diol".

"(4S,2R,3R,5R)-5-[(5-methylisoxazol-3-ylthio)methyl]-2-[6-(cyclopentylamino)purin-9-yl]tetrahydrofuran-3,4-diol".

"(4S,2R,3R,5R)-5-[(3-phenylisoxazol-5-ylthio)methyl]-2-[6-(cyclopentylamino)purin-9-yl]tetrahydrofuran-3,4-diol".

(4S,2R,3R,5R)-2-[(2-phenylethoxy)methyl]-5-[6-(tetrahydrofuran-3-ylamino)purin-9-yl]tetrahydrofuran-3,4-diol;

(4S,2R,3R,5R)-2-[(2-phenylmethoxy)methyl]-5-[6-(tetrahydrofuran-3-ylamino)purin-9-yl]tetrahydrofuran-3,4-diol;

(4S,2R,3R,5R)-2-[5-t-butyl-1,2,4-oxadiazol-3-ylthio)methyl]-5-[6-(cyclopentylamino)-purin-9-yl]tetrahydrofuran-3,4-diol;

(4S,2R,3R,5R)-2-[(3-phenylisoxazol-5-ylmethoxy)methyl]-5-[6-((tetrahydrofuran-3-yl amino)purin-9-yl]tetrahydrofuran-3,4-diol;

(4S,2R,3R,5R)-2-[(3-(4-methoxyphenyl)isoxazol-5-ylmethoxy)methyl]-5-[6-((tetrahydrofuran-3-yl amino)purin-9-yl]tetrahydrofuran-3,4-diol;

(4S,2R,3R,5R)-2-[(3-(4-chlorophenyl)isoxazol-5-ylmethoxy)methyl]-5-[6-((tetrahydrofuran-3-yl amino)purin-9-yl]tetrahydrofuran-3,4-diol;

(4S,2R,3R,5R)-2-[(2-methylthiazol-4-ylmethoxy)methyl]-5-[6-((tetrahydrofuran-3-yl amino)purin-9-yl]tetrahydrofuran-3,4-diol;

(4S,2R,3R,5R)-2-[(5-t-butyl-1,2,4-oxadiazol-3-ylmethoxy)methyl]-5-[6-((tetrahydrofuran-3-yl amino)purin-9-yl]tetrahydrofuran-3,4-diol;

(4S,2R,3R,5R)-2-[1,2,4-oxadiazol-3-ylmethoxy)methyl]-5-[6-((tetrahydrofuran-3-yl amino)purin-9-yl]tetrahydrofuran-3,4-diol;

(4S,2R,3R,5R)-2-[(2-methylthiazol-4-ylmethylthio)methyl]-5-[6-((tetrahydrofuran-3-yl amino)purin-9-yl]tetrahydrofuran-3,4-diol;

(4S,2R,3R,5R)-2-[(5-t-butyl-1,2,4-oxadiazol-3-ylmethylthio)methyl]-5-[6-((tetrahydrofuran-3-yl amino)purin-9-yl]tetrahydrofuran-3,4-diol;

(4S,2R,3R,5R)-2-[(3-(4-chlorophenyl)isoxazol-5-ylmethylthio)methyl]-5-[6-((tetrahydrofuran-3-yl amino)purin-9-yl]tetrahydrofuran-3,4-diol;

(4S,2R,3R,5R)-2-[(3-phenylisoxazol-5-ylmethylthio)methyl]-5-[6-((tetrahydrofuran-3-yl amino)purin-9-yl]tetrahydrofuran-3,4-diol;

(4S,2R,3R,5R)-2-[(3-(4-methoxyphenyl)isoxazol-5-ylmethylthio)methyl]-5-[6-((tetrahydrofuran-3-yl amino)purin-9-yl]tetrahydrofuran-3,4-diol; and (4S,2R,3R,5R)-2-[(3-(3,5-dimethylisoxazol-4-ylmethylthio)methyl]-5-[6-((tetrahydrofuran-3-yl amino)purin-9-yl]tetrahydrofuran-3,4-diol.

C. Preparation of a Compound of Formula I, Varying $R^1$, $R^2$, $R^3$, Y, T, X, and Z Similarly, following the procedure of Example 3A above, but replacing (4S,2R,3R,5R)-2-hydroxymethyl-5-[6-(tetrahydrofuran-3-ylamino)-purin-9-yl]-tetrahydrofuran-3,4-diol acetonide with other compounds of formula (3), and optionally replacing 2-fluorophenol with other compounds of formula $R^3$—YH, other compounds of Formula I are obtained.

EXAMPLE 4

Preparation of a Compound of Formula (9)

Preparation of a Compound of Formula (9) in which $R^1$ is 3-Tetrahydrofuranyl

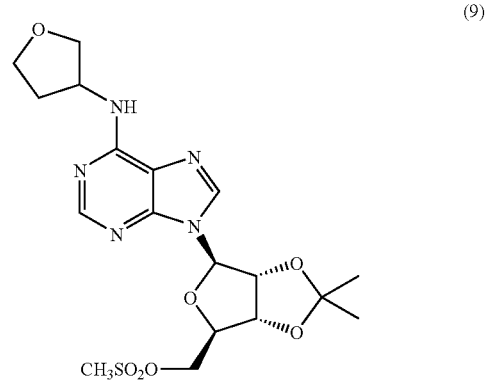

(9)

Step 1 —Preparation of Formula (9)

Methanesulfonyl chloride (0.477 mL; 4.77 mmol) was added dropwise to a solution of 2-hydroxymethyl-5-[6-(tetrahydrofuran-3-yl)-purin-9-yl]-tetrahydrofuran-3,4-diol acetonide, a compound of formula (3) (1.5 g; 3.9 mmol) in dry pyridine (15 ml)cooled to 0° C. The reaction mixture was stirred for 3 hours at 0° C. The solvent was evaporated and the residue dissolved in ethyl acetate (50 mL), washed with water, dried with anhydrous $MgSO_4$, and evaporated to give the compound of formula (9), (4S,2R,3R,5R)-2-hydroxymethyl-5-[6-(tetrahydrofuran-3-yl)-purin-9-yl]-tetrahydrofuran-3,4-diol acetonide 2-methylsulfonate.

EXAMPLE 5

Preparation of a Compound of Formula (10)

Preparation of a Compound of Formula (10) in Which R¹ is 3-Tetrahydrofuranyl

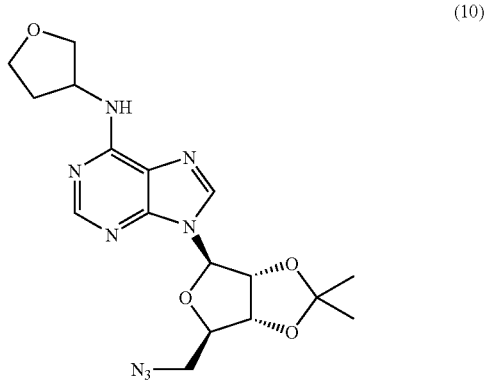

(10)

Sodium azide (300 mg; 4.6 mmol) was added to a solution of (4S,2R,3R,5R)-2-hydroxymethyl-5-[6-(tetrahydrofuran-3-yl)-purin-9-yl]-tetrahydrofuran-3,4-diol acetonide 2-methylsulfonate, a compound of formula (9) (1.4 g; 3 mmol), in dry dimethylformamide (10 mL), and the mixture was heated at 65° C. for 16 hours. The solvent was evaporated and the residue was subjected to aqueous work up and purified by flash column (100% ethyl acetate) to produce (4S,2R,3R,5R)-2-azidomethyl-5-[6-(tetrahydrofuran-3-yl)-purin-9-yl]-tetrahydrofuran-3,4-diol acetonide, a compound of formula (10).

EXAMPLE 6

Preparation of a Compound of Formula (11)

Preparation of a Compound of Formula (11) in which R¹ is 3-Tetrahydrofuranyl

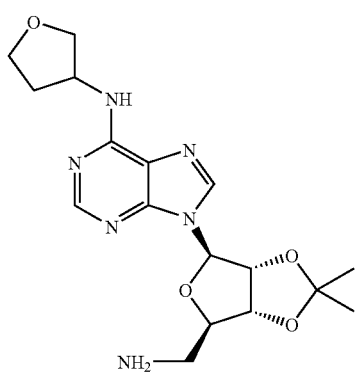

(11)

10%Pd/C (100 mg) was added to a solution of (4S,2R,3R,5R)-2-azidomethyl-5-[6-(tetrahydrofuran-3-yl)-purin-9-yl]-tetrahydrofuran-3,4-diol acetonide, a compound of formula (10) (314 mg), in ethanol (20 mL) and stirred under an atmosphere of hydrogen at room temperature for 16 hours. The catalyst was removed by filtration, and the solvent evaporated from the filtrate to give (4S,2R,3R,5R)-2-aminomethyl-5-[6-(tetrahydrofuran-3-yl)-purin-9-yl]-tetrahydrofuran-3,4-diol acetonide, a compound of formula (11).

EXAMPLE 7

Preparation of a Compound of Formula (12)

Preparation of a Compound of Formula (12) in which R¹ is 3-Tetrahydrofuranyl, R³ is Benzoxazol-2-yl, and T is a Covalent Bond

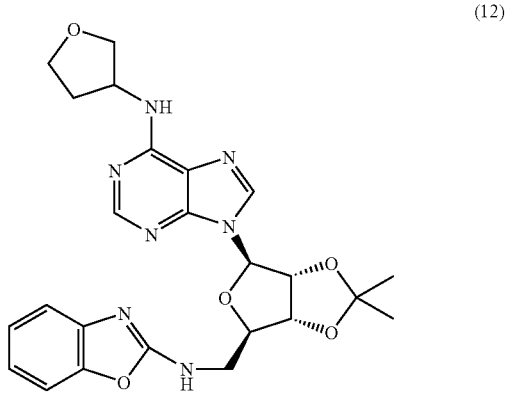

(12)

To a solution of (4S,2R,3R,5R)-2-aminomethyl-5-[6-(tetrahydrofuran-3-yl)-purin-9-yl]-tetrahydrofuran-3,4-diol acetonide, a compound of formula (11) (100 mg), in ethanol (5 mL) was added triethylamine and 2-chlorobenoxazole, and the mixture was refluxed for 16 hours. The solvent was evaporated and the residue purified by preparative TLC (5%MeOH/DCM) to give (4S,2R,3R,5R)-2-(benzoxazol-2-ylaminomethyl)-5-[6-(tetrahydrofuran-3-yl)-purin-9-yl]-tetrahydrofuran-3,4-diol acetonide, a compound of formula (12).

EXAMPLE 8

Preparation of a Compound of Formula I

A. Preparation of a Compound of Formula I in Which R¹ is 3-Tetrahydrofuranyl, R² is Hydrogen, R³ is Benzoxazol-2-yl, Y is —NH—, T and X are both Covalent Bonds, and Z is Methylene

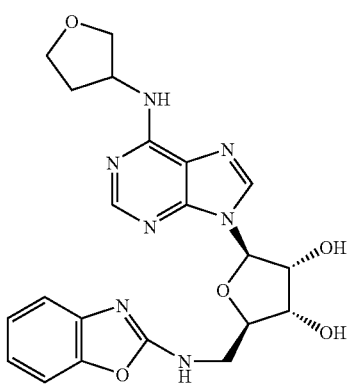

Formula I

A solution of (4S,2R,3R,5R)-2-(benzoxazol-2-ylaminomethyl)-5-[6-(tetrahydrofuran-3-yl)-purin-9-yl]-tetrahydrofuran-3,4-diol acetonide, a compound of formula (12), in 80% acetic acid in water (10 mL) was heated to 80° C. for 16 hours. Solvent was evaporated form the reaction product and the residue was purified by preparative TLC (5%MeOH/DCM) to give (4S,2R,3R,5R)-2-(benzoxazol-2-ylaminomethyl)-5-[6-(tetrahydrofuran-3-yl)-purin-9-yl]-tetrahydrofuran-3,4-diol as a white foam. MS (M+1).

B. Preparation of a Compound of Formula I in Which $R^1$ is Cyclopentyl, $R^2$ is Hydrogen, $R^3$ is Pyrimidin-2-yl or 3-Methylisoxazol-5-yl, Y is —NH—, T and X are both Covalent Bonds, and Z is Methylene Similarly, following the procedures of Examples 4, 5, 6, and 7, optionally replacing (4S,2R,3R,5R)-2-hydroxymethyl-5-[6-(tetrahydrofuran-3-ylamino)-purin-9-yl]-tetrahydrofuran-3,4-diol acetonide with other compounds of formula (12), the following compounds of Formula I in which Y is —NH— were prepared:

2-(pyrimidin-2-ylaminomethyl)-5-[6-cyclopentylaminopurin-9-yl]-tetrahydrofuran-3,4-diol; and 2-(3-methylisoxazol-5-ylaminomethyl)-5-[6-cyclopentylaminopurin-9-yl]-tetrahydrofuran-3,4-diol C. Preparation of a Compound of Formula I Where Y is —NH—, Varying $R^1$, $R^2$, $R^3$, T, X, and Z Similarly, following the procedure of Example 3A above, but replacing (4S,2R,3R,5R)-2-hydroxymethyl-5-[6-(tetrahydrofuran-3-ylamino)-purin-9-yl]-tetrahydrofuran-3,4-diol acetonide with other compounds of formula (12), other compounds of Formula I are obtained.

EXAMPLE 9

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules.

EXAMPLE 10

A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets.

EXAMPLE 11

A dry powder inhaler formulation is prepared containing the following components:

| Ingredient | Weight % |
|---|---|
| Active Ingredient | 5 |
| Lactose | 95 |

The active ingredient is mixed with the lactose and the mixture is added to a dry powder inhaling appliance.

The active ingredient is mixed with the lactose and the mixture is added to a dry powder inhaling appliance.

EXAMPLE 12

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

EXAMPLE 13

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

EXAMPLE 14

Suspensions, each containing 50 mg of active ingredient per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%) | |
| Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

EXAMPLE 15

A subcutaneous formulation may be prepared as follows:

| Ingredient | Quantity |
| --- | --- |
| Active Ingredient | 5.0 mg |
| Corn Oil | 1.0 mL |

EXAMPLE 16

An injectable preparation is prepared having the following composition:

| Ingredients | Amount |
| --- | --- |
| Active ingredient | 2.0 mg/ml |
| Mannitol, USP | 50 mg/ml |
| Gluconic acid, USP | q.s. (pH 5–6) |
| water (distilled, sterile) | q.s. to 1.0 ml |
| Nitrogen Gas, NF | q.s. |

EXAMPLE 17

A topical preparation is prepared having the following composition:

| Ingredients | grams |
| --- | --- |
| Active ingredient | 0.2–10 |
| Span 60 | 2.0 |
| Tween 60 | 2.0 |
| Mineral oil | 5.0 |
| Petrolatum | 0.10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

EXAMPLE 18

| Sustained Release Composition | | | |
| --- | --- | --- | --- |
| Ingredient | Weight Range (%) | Preferred Range (%) | Most Preferred |
| Active ingredient | 50–95 | 70–90 | 75 |
| Microcrystalline cellulose (filler) | 1–35 | 5–15 | 10.6 |
| Methacrylic acid copolymer | 1–35 | 5–12.5 | 10.0 |
| Sodium hydroxide | 0.1–1.0 | 0.2–0.6 | 0.4 |
| Hydroxypropyl methylcellulose | 0.5–5.0 | 1–3 | 2.0 |
| Magnesium stearate | 0.5–5.0 | 1–3 | 2.0 |

The sustained release formulations of this invention are prepared as follows: compound and pH-dependent binder and any optional excipients are intimately mixed(dry-blended). The dry-blended mixture is then granulated in the presence of an aqueous solution of a strong base which is sprayed into the blended powder. The granulate is dried, screened, mixed with optional lubricants (such as talc or magnesium stearate), and compressed into tablets. Preferred aqueous solutions of strong bases are solutions of alkali metal hydroxides, such as sodium or potassium hydroxide, preferably sodium hydroxide, in water (optionally containing up to 25% of water-miscible solvents such as lower alcohols).

The resulting tablets may be coated with an optional film-forming agent, for identification, taste-masking purposes and to improve ease of swallowing. The film forming agent will typically be present in an amount ranging from between 2% and 4% of the tablet weight. Suitable film-forming agents are well known to the art and include hydroxypropyl. methylcellulose, cationic methacrylate copolymers (dimethylaminoethyl methacrylate/methyl-butyl methacrylate copolymers—Eudragit® E—Röhm. Pharma), and the like. These film-forming agents may optionally contain colorants, plasticizers, and other supplemental ingredients.

The compressed tablets preferably have a hardness sufficient to withstand 8 Kp compression. The tablet size will depend primarily upon the amount of compound in the tablet. The tablets will include from 300 to 1100 mg of compound free base. Preferably, the tablets will include amounts of compound free base ranging from 400–600 mg, 650–850 mg, and 900–1100 mg.

In order to influence the dissolution rate, the time during which the compound containing powder is wet mixed is controlled. Preferably the total powder mix time, i.e. the time during which the powder is exposed to sodium hydroxide solution, will range from 1 to 10 minutes and preferably from 2 to 5 minutes. Following granulation, the particles are removed from the granulator and placed in a fluid bed dryer for drying at about 60° C.

EXAMPLE 15

Materials

The $A_1$-adenosine antagonists 8-cyclopentyl-1,3-dipropylxanthine (CPX) and 8-cyclopentyl-1,3-dimethylxanthine (CPT), the $A_1$-adenosine agonists $N_6$-cyclopentyladenosine (CPA), 2-chloro-$N_6$-cyclopentyladenosine (CCPA), and-$N_6$-cyclohexyladenosine (CHA), the adenosine deaminase inhibitor erythro-9-(2-hydroxy-3-nonyl)adenine (EHNA), the adenosine kinase inhibitor iodotubercidin, and forskolin were purchased from Research Biochemicals (Natick, Mass.). {[(5-{6-[(3R)oxolan-3-yl]amino} purin-9-yl)(3S, 2R,4R)-3,4-di-hydroxyoxolan-2-yl]-methoxy}-N-methylcarboxamide, molecular weight 394.38, is a derivative of the selective $A_1$-adenosine receptor full agonist CVT-510 and was synthesized at CV Therapeutics by co-authors J. A. Zablocki and V. Palle. Adenosine was purchased from Sigma Chemical (St. Louis, Mo.). The radioligand 8-cyclopentyl-1,3-dipropyl-[2,3-$^3$H(N)]xanthine ([$^3$H]CPX) was purchased from New England Nuclear (Boston, Mass.). Concentrated stock solutions (10–100 mM) of CVT-2759, CPX, CPT, CPA, CCPA, CHA, and forskolin were dissolved in dimethylsulfoxide, stored as aliquots at −80° C., and diluted in physiological saline for use in experiments. The final content of dimethylsulfoxide in saline during experiments was not more than 0.1%. Adenosine and EHNA were dissolved in saline immediately before use.

BINDING ASSAYS—$DDT_1$ CELLS

Cell Culture

DDT cells (hamster vas deferens smooth muscle cell line) were grown as monolayers in petri dishes using Dulbecco's Modified Eagle's Medium (DMEM) containing 2.5 µg ml$^{-1}$ amphotericin B, 100 U ml$^{-1}$ penicillin G, 0.1 mg ml$^{-1}$ streptomycin sulfate and 5% fetal bovine serum in a humidified atmosphere of 95% air and 5% $CO_2$. Cells were subcultured twice weekly by dispersion in Hank's Balanced Salt Solution (HBSS) without the divalent cations and containing 1 mM EDTA. The cells were then seeded in growth medium at a density of $1.2 \times 10^5$ cells per plate and experiments were performed 4 days later at approximately one day preconfluence.

Membrane Preparations

Cell layers were washed twice with HBSS (2×10 ml), scraped free of the plate with the aid of a rubber policeman in 5 ml of 50 mM Tris-HCl buffer pH 7.4 at 4° C. and the suspension homogenized for 10 s. The homogenate was centrifuged at 27,000×g for 10 min, resuspended in buffer, and centrifuged again, as described above. The protein content was determined with a Biorad Protein Assay Kit (Richmond, Calif.) using bovine serum albumin as standard. This membrane suspension was stored dimethylsulfoxide (DMSO) in He buffer (10 mM HEPES, 1 uM EDTA at pH 7.4) and stored in liquid nitrogen at −80° C.

Competitive Binding Assays

Compounds of Formula I were assayed to determine their affinity for the $A_1$ adenosine receptor sites on the membranes of DDT cells. Briefly, 50–70 ug of membrane protein were incubated in a mixture containing 2U/ml adenosine deaminase, 10 mM GTP-γS in 5 mM HE buffer containing 5 mM $MgCl_2$ in glass tubes Stock solutions of the compounds of the invention were serially diluted ($10^{-10}$M to $10^{-4}$M) in HE buffer or HE buffer alone (control to determine non-specific binding) and added to the incubation mixture. Finally, tritiated 8-cyclopentyladenosine ($^3$H-CPX) was added to a final concentration of 1.5 nM. After incubation at 23° C. 90 minutes, the reaction was stopped by filtration on a Brandel MR24 cell harvester and washing with ice-cold Tris-EDTA buffer (three times, approximate volume 10 ml/wash) over Whatman GF/B filters (presoaked for 1 h in 0.3% polyethylenimine to reduce non-specific binding). Filters were transferred to scintillation vials and 5 ml of Scintisafe (VWR, Brisbane, Calif.) was added. The amount of radioactivity retained on the filters was determined by liquid scintillation spectrometry. Protein determinations were by the method of Bradford (1976. Anal. Biochem. 72:248) using bovine serum albumin as the standard. Results are expressed as means of triplicates+SEM after subtracting amount of radioactivity due to non-specific binding.

EXAMPLE 16

[$^{35}$S]GTPγS Binding Assays

The ability of agonists to activate G proteins was determined by using radiolabed GTP ([$^{35}$S]GTPγS). Briefly, membrane proteins (30–50 µg/assay tube) were placed in glass tubes containing 50 mM Tris-HCl buffer pH 7.4, 5 MM $MgCl_2$, 100 mM NaCl, 1 mM dithiothreitol, 0.2 units ml$_{-1}$ adenosine deaminase, 0.5% BSA, 1 mM EDTA, 10 mM GDP, and 0.3 nM [$^{35}$S]GTPγS. Varying concentrations of the compounds of the invention (putative $A_1$ adenosine receptor agonists), a known $A_1$ adenosine receptor full agonist N cyclopentlyladenosine (CPA) or a control tube containing 10 uM GTPγS but no agonist (to determine nonspecific binding) were added to separate tubes. The assay tubes were incubated for 90 min at 37° C. Agonist stimulated binding was assessed by determining the difference between total binding in the presence of putative agonists and basal binding determined in the absence of CPA. Results were expressed as the percentage stimulation of the putative agonists relative to the full agonist CPA after subtracting out non-specific binding.

Guinea Pig Isolated Perfused Hearts

Guinea pigs (Hartley) of either sex weighing 300–350 g were anaesthetized with methoxyflurane and killed by decapitation. The chest was cut open, and the heart was quickly removed and rinsed in ice-cold modified Krebs-Henseleit (K-H) solution. The contents of the modified K-H solution were (in mM) 117.9 NaCl, 4.8 KCl, 2.5 $CaCl_2$, 1.18 $MgSO_2$, 1.2 $KH_2PO_4$, 0.5 $Na_2$ EDTA, 0.14 ascorbic acid, 5.5 dextrose, 2.0 pyruvic acid (sodium salt), and 25 $NaHCO_3$. The K-H solution was continuously gassed with 95% $O_{2-5}$% $CO_2$, and the pH was adjusted to a value of 7.4. To perfuse the heart by the Langendorff method, the transected aorta was slid onto a glass cannula and secured by a ligature. Retrograde perfusion of the aorta was initiated immediately at a constant flow of 10 ml/min with modified K-H solution warmed to 36.0±0.5° C. A side port in the cannula was used to connect the perfusion line to a Gould pressure transducer for measurement of coronary perfusion pressure. Coronary perfusion pressure was continuously recorded on a strip chart (Gould RS3400, Cleveland, Ohio) throughout each experiment. Coronary conductance (in ml min$^{-1}$ mmHg-1) was calculated as the ratio of coronary flow (10 ml/min) to perfusion pressure (in mmHg). To facilitate the exit of fluid from the left ventricle, the leaflets of the mitral valve were trimmed with fine spring-handled scissors. When appropriate, hearts were paced at a constant rate using external electrodes. After completion of dissection and instrumentation, stimulus-to-His bundle (S-H) interval and coronary perfusion pressure was monitored continuously, each heart was allowed to equilibrate for 20–40 min before the administration of drug. Experimental interventions were always preceded and followed by control measurements. Criteria for the exclusion of hearts from the study were 1) a coronary perfusion pressure of <50 mmHg, 2) absence of a stable coronary perfusion pressure during the equilibration period, and 3) inability to pace a heart at a constant rate throughout an experiment.

For electrical pacing of hearts, a bipolar Teflon-coated electrode was placed in the wall of the intra-atrial septum. Parts of the left and right atrial tissues, including the region of the sinoatrial node, were removed, both to decrease the spontaneous heart rate and to expose the atrial septum for electrode placement. Hearts were electrically paced at a fixed rate of 3.2 HZ. Stimuli were provided by an interval generator (model 1830, WPI, Sarasota, Fla.) and delivered through a stimulus isolation unit (model 1880, WPI) as square wave pulses of 3 ms in duration and at least twice the threshold intensity.

S-H interval. Prolongation of the S-H interval was used as a measure of the negative dromotropic effect of $A_1$-adenosine agonists on AV nodal conduction. The His bundle electrogram was recorded from a unipolar electrode placed in the right side of the interatrial septum adjacent to the AV junction. The signal was displayed continuously in real time on an oscilloscope screen at a sweep rate of 10 ms/cm. The duration of time from the first pacing artifact to the maximum upward deflection of the His bundle signal was used as the S-H interval.

Hearts were equilibrated until the S-H interval and CPP remained constant. Drug was used to the perfused line in a final concentration of 0.3, 3, 10 and in some heart up to 30 μM. If the second degree AV block happened at any concentration before 30 μM, the drug was withdraw to washout. After washout the first compound, the second compound only could be used in a same heart unless the SH interval and CPP came back to the control or S-H interval prolonged less than 2 ms compared to the control. Up to three compounds could be used in a same heart.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. All patents and publications cited above are hereby incorporated by reference.

What is claimed is:

1. A compound of Formula I:

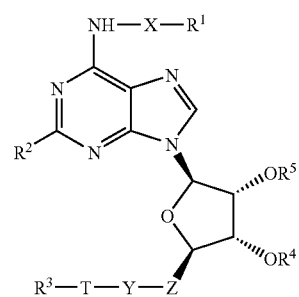

Formula I wherein:
$R^1$ is 3-tetrahydrofuranyl:
$R^2$ is hydrogen;
$R^3$ is phenyl optionally substituted by halo or lower alkyl of 1–4 carbon atoms or is chosen from the group consisting of benzothiazolyl optionally substituted by lower alkyl of 1–4 carbon atoms, berizoxazolyl, pyridinyl, benzofuranyl, 4-quinolinyl, 5-isoquinalinyl, isoxazolyl optionally substituted by lower alkyl of 1–4 carbon atoms, and 1,2,4-oxadiazolyl optionally substituted by lower alkyl of 1–4 carbon atoms;
$R^4$ and $R^5$ are independently hydrogen or acyl;
T and X are independently a covalent bond or alkylene of 1–3 carbon atoms;
Y is —O— or —NH—; and
Z is alkylene of 1–3 carbon atoms.

2. The compound of claim 1, wherein $R^4$ and $R^5$ are hydrogen and Y is —O—.

3. The compound of claim 2, wherein X is a covalent bond.

4. The compound of claim 3, wherein Z is methylene.

5. The compound of claim 4, wherein $R^3$ is 5-methylisoxazol-3-yl and T is a covalent bond, namely (4S,2R,3R,5R)-2-[(5-methylisoxazol-3-yloxy)methyl]-5-[6-(tetrahydrofuran-3-ylamino)purin-9-yl]tetrahydrofuran-3,4-diol.

6. The compound of claim 4, wherein $R^3$ is phenyl optionally substituted by halo or lower alkyl of 1–4 carbon atoms and T is a covalent bond.

7. The compound of claim 6, wherein $R^3$ is 2-fluorophenyl, namely (4S,2R,3R,5R)-2-(2-fluorophenoxymethyl)-5-[6-(tetrahydrofuran-3-ylamino)-purin-9-yl]-tetrahydrofuran-3,4-diol.

8. The compound of claim 6, wherein $R^3$ is 2-chlorophenyl, namely (4S,2R,3R,5R)-2-(2-chlorophenoxymethyl)-5-[6-(tetrahydrofuran-3-ylamino)-purin-9-yl]-tetrahydrofuran-3,4-diol.

9. The compound of claim 6, wherein $R^3$ is 4-fluorophenyl, namely (4S,2R,3R,5R)-2-(4-fluorophenoxymethyl)-5-[6-(tetrahydrofuran-3-ylamino)-purin-9-yl]-tetrahydrofuran-3,4-diol.

10. The compound of claim 6, wherein $R^3$ is 3-fluorophenyl, namely (4S,2R,3R,5R)-2-(3-fluorophenoxymethyl)-5-[6-(tetrahydrofuran-3-ylamino)-purin-9-yl]-tetrahydrofuran-3,4-diol.

11. The compound of claim 6, wherein $R^3$ is 2-methylphenyl, namely (4S,2R,3R,5R)-2-(2-methylphenoxymethyl)-5-[6-(tetrahydrofuran-3-ylamino)-purin-9-yl]-tetrahydrofuran-3,4-diol.

12. The compound of claim 1, wherein $R^4$ and $R^5$ are hydrogen and Y is —NH—.

13. The compound of claim 12, wherein X is a covalent bond, and Z is methylene.

14. The compound of claim 13, wherein $R^3$ is 3-methylisoxazolin-5-yl and T is a covalent bond.

15. A pharmaceutical composition comprising a pharmaceutically acceptable excipient and a therapeutically effective amount of a compound of claim 1.

* * * * *